United States Patent
Raulerson et al.

(10) Patent No.: US 8,403,891 B2
(45) Date of Patent: Mar. 26, 2013

(54) METHOD FOR CENTERING A VALVE

(75) Inventors: J. Daniel Raulerson, Brewton, AL (US);
Mark S. Fisher, Sellersville, PA (US);
W. Shaun Wall, North Wales, PA (US)

(73) Assignee: Medical Components, Inc., Harleysville, PA (US)

(*) Notice: Subject to any disclaimer, the term of this patent is extended or adjusted under 35 U.S.C. 154(b) by 0 days.

(21) Appl. No.: 13/207,019

(22) Filed: Aug. 10, 2011

(65) Prior Publication Data

US 2011/0289759 A1 Dec. 1, 2011

Related U.S. Application Data

(62) Division of application No. 12/469,839, filed on May 21, 2009, now Pat. No. 8,052,647.

(60) Provisional application No. 61/055,005, filed on May 21, 2008.

(51) Int. Cl.
*A61M 5/178* (2006.01)

(52) U.S. Cl. .................................. 604/167.03

(58) Field of Classification Search ............... 604/167.02–167.06; 251/149.1, 251/159, 170
See application file for complete search history.

(56) References Cited

U.S. PATENT DOCUMENTS

| | | | |
|---|---|---|---|
| 4,269,186 A | 5/1981 | Loveless et al. | |
| 4,387,879 A | 6/1983 | Tauschinski | |
| 4,512,766 A | 4/1985 | Vailancourt | |
| 4,813,938 A | 3/1989 | Raulerson | |
| 4,842,591 A | 6/1989 | Luther | |
| 5,045,065 A | 9/1991 | Raulerson | |
| 5,062,836 A | 11/1991 | Wendell | |
| 5,085,645 A | 2/1992 | Purdy et al. | |
| 5,104,381 A | 4/1992 | Gresl et al. | |
| 5,269,771 A | 12/1993 | Thomas et al. | |
| 5,336,192 A | 8/1994 | Palestrant | |
| 5,441,487 A | 8/1995 | Vedder | |
| 5,584,808 A | 12/1996 | Healy | |
| 5,788,215 A | 8/1998 | Ryan | |
| 5,911,710 A | 6/1999 | Barry et al. | |
| 5,980,492 A | 11/1999 | Rosen et al. | |
| 6,024,729 A | 2/2000 | Dehdashtian et al. | |
| 6,277,100 B1 * | 8/2001 | Raulerson et al. | 604/212 |

(Continued)

FOREIGN PATENT DOCUMENTS

| | | |
|---|---|---|
| EP | 0353905 A1 | 2/1990 |
| WO | 9945996 A1 | 9/1999 |

OTHER PUBLICATIONS

International Search Report dated Jun. 10, 2009 in connection with international application No. PCT/US2009/044765 (5 pages).

(Continued)

*Primary Examiner* — Nicholas Lucchesi
*Assistant Examiner* — Pritesh Patel
(74) *Attorney, Agent, or Firm* — Glenn M. Massina, Esq.; Fox Rothschild LLP

(57) ABSTRACT

A vascular guidewire introducer device (10) having a needle (52), a bulb (16), and a valve subassembly (100) through which a guidewire (14) is insertable for vascular guidewire insertion into a blood vessel (12) of a patient. The valve subassembly (100) includes a proximal fitting (102), a proximal cap (106), and a valve arrangement (104) disposed within a valve seat (118) defined by one of the fitting and the cap. The valve arrangement includes distal and proximal disc-shaped valve members (122,126) having centered slits (124,128) therethrough, and a spacer (130) disposed between the valve members. A method is disclosed for precisely centering the slits of the valve members during assembly and for retaining the valve members in their precisely centered positions in the valve seat. The valve arrangement permits use with a wide range of guidewire diameters.

2 Claims, 4 Drawing Sheets

U.S. PATENT DOCUMENTS

| | | | |
|---|---|---|---|
| 6,352,521 B1 | 3/2002 | Prosl | |
| 6,488,674 B2 | 12/2002 | Becker et al. | |
| 7,008,404 B2 | 3/2006 | Nakajima | |
| 7,081,106 B1 * | 7/2006 | Guo et al. | 604/167.06 |
| 7,470,254 B2 | 12/2008 | Basta et al. | |
| 2004/0143219 A1 | 7/2004 | Lee et al. | |
| 2004/0215146 A1 * | 10/2004 | Lampropoulos et al. | 604/168.01 |

OTHER PUBLICATIONS

Written Opinion dated Jun. 10, 2009 in connection with international application No. PCT/US2009/044765 (6 pages).

International Preliminary Report on Patentability issued on Apr. 15, 2011 in connection with international application No. PCT/US2009/47765 (10 pages).

* cited by examiner

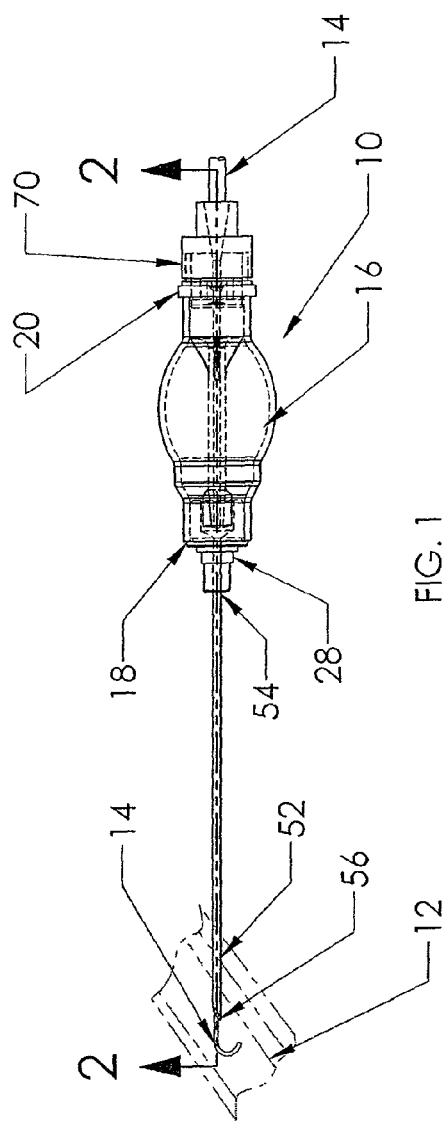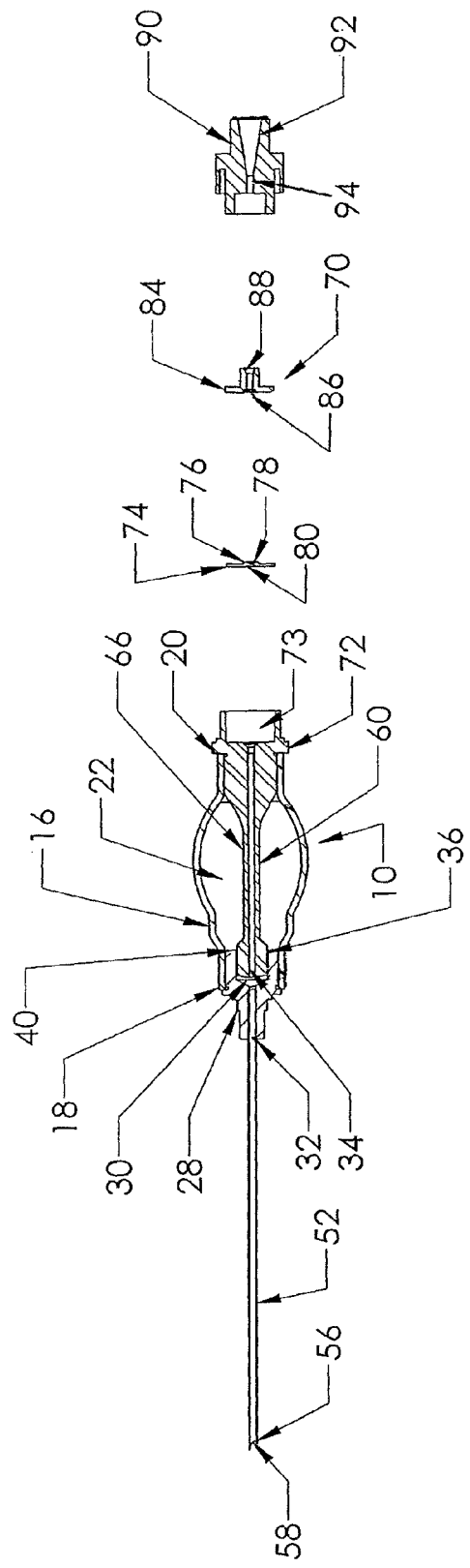

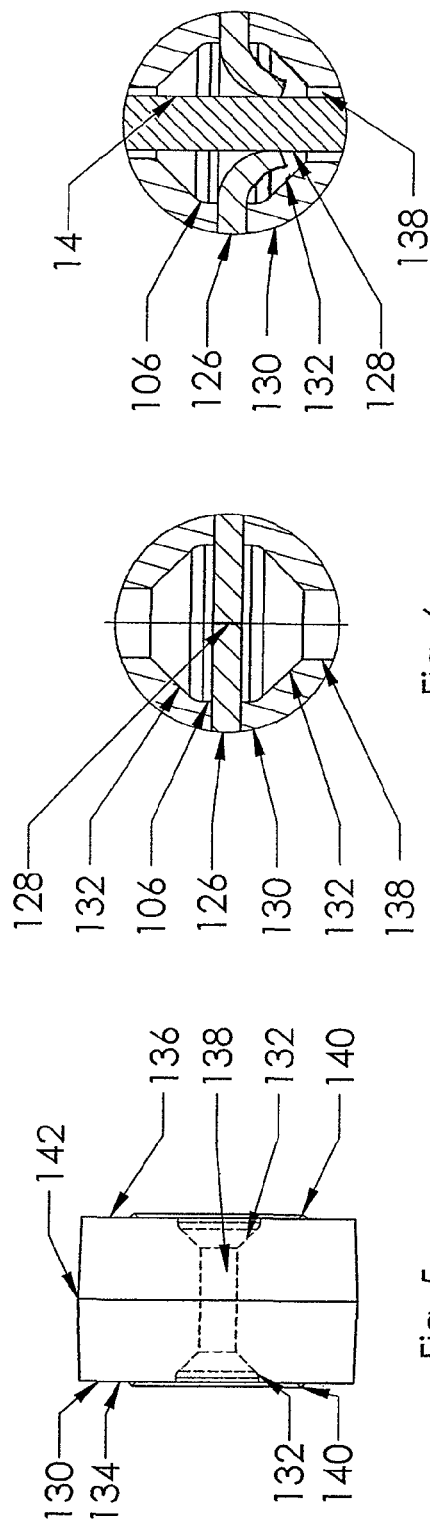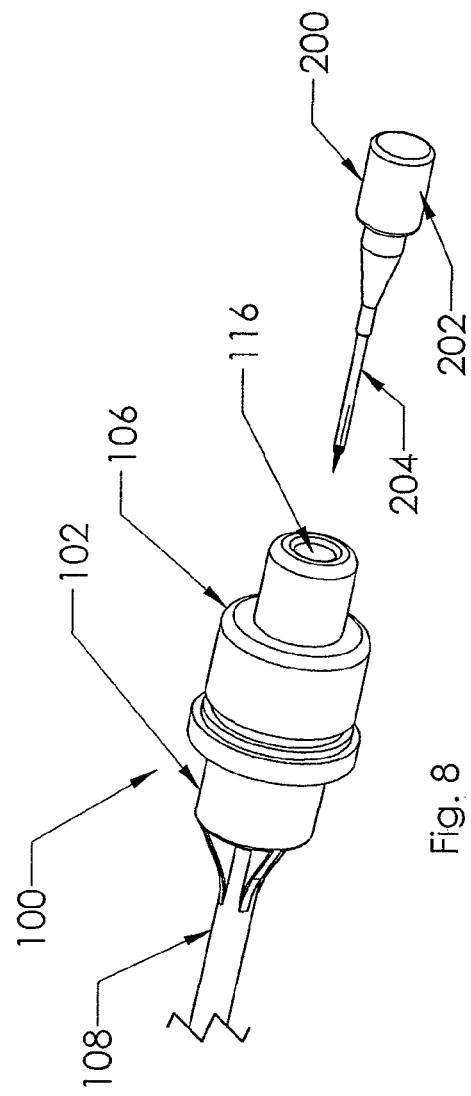

METHOD FOR CENTERING A VALVE

CROSS-REFERENCE TO RELATED APPLICATIONS

This application is a Divisional application of U.S. application Ser. No. 12/469,839 filed May 21, 2009, which claims priority from U.S. Provisional Application Ser. No. 61/055,005, filed May 21, 2008.

FIELD OF THE INVENTION

This relates to the field of medical devices and more particularly to vascular guidewire introducer devices.

BACKGROUND OF THE INVENTION

Generally, to insert any catheter into a blood vessel, the vessel is identified by aspiration with a long hollow needle in accordance with the well known Seldinger technique. In its simplest application, a needle, with a syringe attached, is introduced into the patient. When blood enters the syringe, it provides visual indication that the vessel has been found; the syringe is then disconnected from the needle and a thin guidewire is then introduced into the needle and into the interior of the vessel. Commonly, upon disconnection of the syringe from the needle, bleeding can occur from the needle and onto the operative field, or air can be aspirated into the vessel if the patient inspires while the needle is not sealed prior to and during introduction of the guidewire into the needle. Blood on the operative field exposes the caregivers to contamination with blood-borne pathogens, and intravascular air can result in vascular occlusion and injury or death. The introducer needle is then removed from the patient and slid over the guidewire proximal end, leaving the distal end portion of the guidewire that has been inserted into the vessel within the vessel and the opposing end of the guidewire projecting beyond the surface of the skin of the patient.

At this point, several options are available to a physician for catheter placement. The simplest is to pass a catheter into the vessel directly over the guidewire. The guidewire is then removed, leaving the catheter in position within the vessel. However, this technique is only possible in cases where the catheter is of relatively small diameter, made of a stiff material, and not significantly larger than the guidewire. For example, this technique may be used to insert small single-lumen or dual-lumen catheters into a patient. If the catheter being inserted is significantly larger than the guidewire, a dilator catheter made of stiff material is passed over the guidewire to enlarge the hole. The dilator catheter is then removed, and the catheter is then passed over the guidewire into the vessel after which the guidewire is then removed.

One type of syringe and needle for use in introducing a guidewire into the vasculature is disclosed in U.S. Pat. No. 5,045,065. The syringe assembly includes a syringe barrel to which a distally projecting needle can be attached. The barrel contains a fluid chamber, and a tube attached to the distal base of the barrel projects proximally into the chamber and includes a proximal side hole within the barrel. A two-part plunger is slidable within and along the chamber and contains a centrally located guidewire passage therethrough; the proximal end of the tube also extends into the plunger's guidewire passage. A valve assembly is contained within the plunger near its proximal end and includes a pair of axially staggered valves within the plunger and traversing the guidewire passage to prevent fluid flow therethrough from the needle, or air passing therethrough from the open plunger proximal end, while permitting insertion therethrough of the guidewire.

In use, regarding the device of U.S. Pat. No. 5,045,065, the vessel is identified by first inserting the distal tip of the needle below the skin. The plunger is then withdrawn proximally to develop negative pressure within the barrel of the syringe. Traction on the plunger is then maintained while the syringe is advanced into the vessel. Upon the needle's distal tip entering the blood vessel, blood is aspirated into the syringe barrel through the side hole of the tube within the barrel's chamber. Once the vessel is identified, the plunger is advanced and aspirated blood is flushed back into the vessel. The guidewire is then inserted through the plunger and the valve assembly, through the guidewire passage tube in the barrel, through the needle and into the vessel of the patient.

Although the device of U.S. Pat. No. 5,045,065 represents a significant improvement over the standard syringe/needle technique as taught by Seldinger, its use has several drawbacks: (1) the plunger must be retracted as the syringe is advanced in the opposite direction; (2) the syringe is heavy and once the needle is in the vessel it must be supported by one hand of the practitioner, allowing only one hand for preparation and introduction of the guidewire; (3) even with the plunger seated within the barrel of the syringe, the distance from the guidewire entry into the plunger to the vessel is relatively long, and any inadvertent movement of the syringe during the procedure can dislodge the needle from the vessel; and, (4) negative pressure created by the practitioner as the syringe is advanced is operator-dependent and even though non-coring needles are used, if the negative pressure is too high, subcutaneous fat can be pulled into the needle causing occlusion and preventing blood entry into the barrel even when the needle enters the vessel.

In U.S. Pat. No. 6,277,100 is disclosed an introducer device that includes an integral aspiration bulb and no plunger, which disclosure is incorporated hereinto by reference. Such a closed system vascular guidewire introducer device is illustrated in FIGS. 1 and 2 hereof. The device includes a transparent flexible valved bulb to which a needle is removably attached at its distal end. A conduit extends from the proximal device end and through the bulb, and is aligned with the needle's channel, thus defining a passageway extending through the device for eventual insertion of a guidewire therethrough into the vasculature. The conduit includes a proximal valve traversing the conduit at the proximal end of the bulb, the valve being openable by the guidewire being inserted therethrough but otherwise remaining closed to seal the conduit. The device is operated by first compressing the bulb. The needle is then inserted under the skin and the pressure on the flexible bulb is released creating constant negative pressure on the needle. The device is then advanced into the blood vessel, and once the needle tip enters the blood vessel, blood is aspirated into the bulb by the negative pressure created on the flexible bulb. A guidewire is then introduced and passed through the valve contained within the bulb assembly and advanced into the vessel. The bulb and needle are then removed leaving the guidewire within the vessel. The advantages of this device are as follows: (1) the negative pressure necessary for aspiration of blood is not operator dependent but rather is maintained by the bulb once it is compressed and released; (2) the device is lightweight and in most adults does not require the practitioner to support it once the vessel is identified; and, (3) the length of the device is shorter than the syringe/needle combination described in the previous patent. Therefore, with these advantages, there is less likelihood of losing cannulation during the procedure.

Guidewires usually are tightly coiled wires that are known for their flexibility, and they range in size from about 0.018 in (0.457 mm) to 0.045 in (1.143 mm), with the smaller size guidewires being more flexible than the larger sizes. While the valve of the above-referenced bulb introducer permits passage of guidewires of most sizes, the valve has proven to be relatively stiff, and too often resists the insertion therethrough of guidewires of very small size, such as 0.018 in, which are known to be highly flexible. Further, even after insertion, the valve compresses against the guidewire to establish noticeable friction, or drag, that inhibits the practitioner from reliance on delicate tactile feel of the guidewire's contact with the vessel walls of the patient's vasculature.

It is desired to provide a valve or valve arrangement for a guidewire introducer device that facilitates smooth insertion of a guidewire through the valve or valve arrangement with minimal friction or drag and without snagging or damaging the valve, and permitting both advancement or retraction of the guidewire therethrough during guidewire placement, with minimal friction or drag and without snagging or causing valve damage. The valve must also reseal prior to insertion to maintain the negative pressure created when the bulb is compressed prior to insertion under the skin and then released after insertion.

It is also desired to provide the guidewire introducer device with such a valve for use with, and to permit successful insertion through the valve assembly of, especially small diameter guidewires, such as 0.018 in (0.457 mm), as well as larger diameter guidewires, such as 0.045 in (1.143 mm).

It is further desired to permit enhanced tactile feel transmitted by the guidewire to the practitioner, that is desired by the practitioner during guidewire placement through the vasculature, again especially with very small diameter guidewires.

BRIEF SUMMARY OF THE INVENTION

Briefly, the present invention is an introducer device for vascular guidewire insertion, having a valve arrangement that permits and facilitates smooth guidewire insertion therethrough with minimal friction, without snagging and without valve damage. The introducer device includes a bulb mounted on distal and proximal fittings. A needle is mounted to the distal fitting to extend distally from the bulb. The introducer device of the present invention includes a conduit that extends integrally from the proximal fitting through the bulb to the distal fitting and is aligned with the passageway of the needle, with an opening into the bulb at the distal fitting for blood aspiration into the bulb. A proximal cap is affixed to the proximal fitting and retains a valve arrangement within a valve seat defined by at least one of the proximal cap and the proximal fitting, the valve arrangement being normally closed but permitting insertion therethrough of a guidewire upon its insertion into an entrance of the proximal cap.

The valve arrangement of the present invention comprises a single valve such as of elastomeric material, or more preferably a pair of valves spaced apart from each other by a spacer, all of which are secured within the valve seat. Preferably, the or each valve is a thin disc with a slit partially traversing the disc at its center. Also, preferably, the transverse disc-adjacent surfaces of the proximal fitting, the spacer and the proximal cap include small funnel-shaped depressions thereinto to facilitate insertion of the guidewire through the device and also provide clearance for deflection of slit-adjacent lips of the valve member or members during guidewire insertion, and facilitates advancement of the guidewire and retraction thereof, if necessary.

Precision centering of the valve members with respect to the axis of the introducer device is preferable, such that the or each slit precisely intersects the axis. Centering may be performed such as with a centering tool prior to firmly fixing the respective positions of the valve members within the device, as follows: the valve members are placed in the valve seat and are of a smaller diameter than the valve seat to permit incremental transverse adjustment, and the spacer is also positioned in the valve seat between the valve members; prior to fully positioning the proximal cap onto the proximal fitting, a mandrel of the centering tool is inserted through the proximal cap, through the slit of the proximal valve member, through the axial bore of the spacer and through the slit of the distal valve member and into the passageway of the proximal fitting, which precisely centers the valves in the valve seat; with the centering tool in its inserted position, the proximal cap is urged completely onto the proximal fitting, compressing the valve members between the adjacent surfaces of the proximal fitting, the spacer and the proximal cap, and the proximal cap is bonded or welded in position, or otherwise permanently affixed to the proximal fitting; the centering tool is then withdrawn.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a longitudinal elevation view of a PRIOR ART guidewire introducer device extending into a blood vessel, with a guidewire extending therethrough;

FIG. 2 is a longitudinal cross-sectional, exploded view of the PRIOR ART introducer device of FIG. 1 taken along lines 2-2 with the guidewire removed;

FIG. 5 is an elevation view of the valve separator of the present invention;

FIGS. 6 and 7 are enlarged views of the valve seat of the present invention illustrating the insertion of a guidewire through a valve member, with FIG. 6 showing the valve slit region and FIG. 7 showing a guidewire being inserted through the valve slit;

FIG. 8 is an isometric view of the proximal end assembly of the present invention, with a valve centering tool positioned to be inserted thereinto for centering the valves;

DETAILED DESCRIPTION OF THE INVENTION

Figure 3:
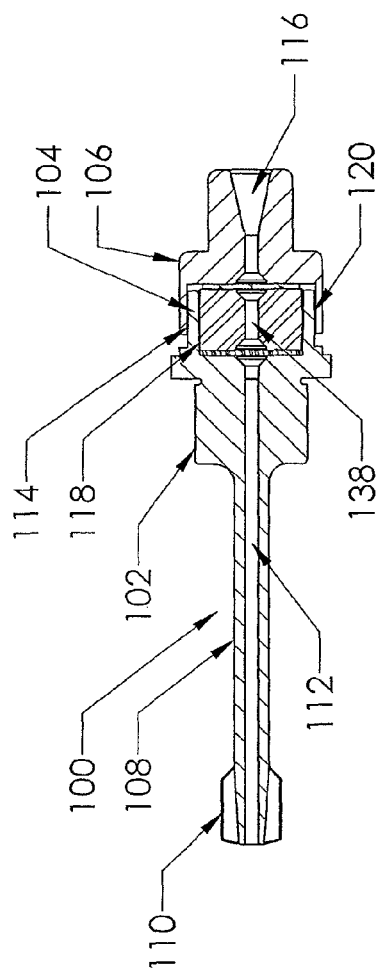
FIG. 3 is a longitudinal cross-sectional view of the proximal end assembly of an introducer device containing the valve arrangement of the present invention.

In the drawings, like numerals indicate like elements throughout. Certain terminology is used herein for convenience only and is not to be taken as a limitation on the present invention. The terms "distal" and "proximal" refer, respectively, to directions closer to and away from a patient's blood vessel. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

As shown in FIGS. 1 and 2, generally, a PRIOR ART guidewire introducer device 10 is used to aspirate a blood vessel 12 (shown in phantom), and insertion of a guidewire 14 into the blood vessel. The guidewire may be straight or have a J-shaped insertion end to prevent the end of the guidewire 14 from catching on the inner wall of the blood vessel 12. A flexible bulb 16 of transparent material includes a first end 18, a second end 20 and an interior cavity 22. A distal fitting 28 is located on the first end 18 of the bulb and includes an internal chamber 30, and first and second axially aligned passageways 32,34 in fluid communication with the chamber 30. A third passageway 36 is provided in the distal fitting 28 in fluid communication between the chamber 30 and the interior cavity 22 of the bulb 16.

An introducer needle 52 has distal and proximal ends 56,54 and a lumen 58, and the distal end 56 is sharpened to allow for penetration of blood vessel 12, as shown in FIG. 1. The proximal end of the needle is connected to the fitting 28 in the first passageway 32 to be in fluid communication with the lumen 58, and chamber 30 is funnel-shaped to facilitate guidewire insertion into the proximal end of lumen 58.

The PRIOR ART valve subassembly includes a proximal fitting 72, a proximal cap 90 and a valve assembly 70. Proximal fitting 72 is affixed within the second end 20 of the bulb 16 and includes a conduit portion 60 extending integrally distally through the bulb to conclude in a plug 40 seated in chamber 30. A passageway 66 extends through the proximal fitting 70 and the conduit portion 60 to open into second passageway 34 and the internal chamber 30 whereat it is in alignment with lumen 58 of the needle. Plug 40 includes one or more axial channels located radially outwardly of passageway 66 that provide fluid communication between chamber 30 and interior cavity 22 of bulb 16.

Proximal cap 90 is affixed to proximal fitting 72 and secures in a valve seat 73 defined therebetween, a valve assembly 70. Cap 90 includes a funnel-shaped entrance 92 and an axial bore 94 aligned with the conduit passageway 66, and the valve assembly 70 is disposed to traverse the region between the axial bore 94 and passageway 66. The valve assembly 70 of the PRIOR ART shown in FIGS. 1 and 2 comprises a seal 74 and a seal support 84, where the seal has a raised portion 76 around the center of the proximal surface, a depression 78 therewithin, and a slit 80 across the center of the depression. Seal support 84 includes a recess 86 complementary to raised seal portion 76, and has a central opening 88 aligned with slit 80 such that a guidewire 14 is insertable through the central opening 88 and slit 80 to extend from the axial bore 94 to enter the conduit passageway 66 and thus into the chamber 30 of the distal fitting 28 and into the lumen 58 of the needle.

Figure 4:
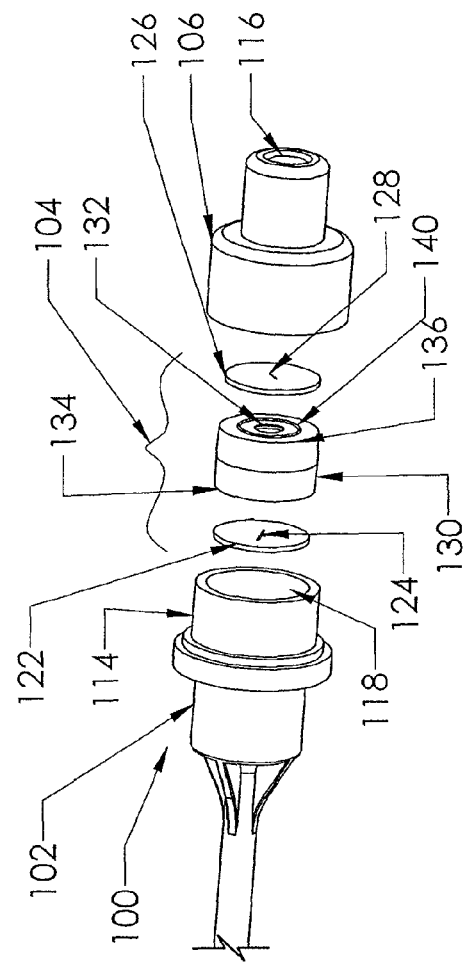
FIG. 4 is an exploded isometric view of the proximal end assembly of FIG. 3.

The present invention is shown generally in FIGS. 3 and 4, and comprises a valve subassembly 100 for a guidewire introducer device, that includes a proximal fitting 102, a valve arrangement 104 and a proximal cap 106. Proximal fitting 102 has a conduit portion 108 extending to a distal plug portion 110, and a passageway 112 therethrough from a proximal flange 114; conduit and plug portions 108,110 can be those of the PRIOR ART conduit portion 60 and plug 40.

Proximal cap 106 includes an entrance 116 that is in alignment with conduit passageway 112. Valve arrangement 104 is disposed within a valve seat 118 and is secured therein by proximal cap 106, and the valve seat may be defined in one of the proximal fitting and the proximal cap, and is shown as being defined in the proximal flange 114 of the proximal fitting 102. The proximal fitting and the proximal cap have transverse valve-adjacent surfaces bounding the valve seat to compress the valves axially upon complete assembly. The proximal flange is received into a distal recess 120 of proximal cap and affixed thereto, after the valve arrangement has been assembled and centered in valve seat 118.

Valve arrangement 104 preferably includes a pair of valve members 122,126 each having a central opening therethrough, such as a slit 124,128 traversing a central portion that permits insertion therethrough of a guidewire (see FIG. 1). It is desirable that the valve members are so positioned in the valve seat that the slits 124,128 are relatively angularly offset (see FIG. 4). Preferably, each valve member 122,126 is a thin flat disc of elastomeric material such as polyisoprene. Between valve members 122,126 is a spacer 130 of relatively noncompressible material having a central funnel-shaped depression 132 into each of the proximal surface 134 and the distal surface 136, each defining an entrance into an axial bore 138 that extends through the spacer between the depressions (see FIG. 5). The central funnel-shaped depression 132 is adapted to facilitate capture of the tip of the guidewire and direct it into the axial bore 138, similarly to the funnel-shaped depression into the body of proximal fitting 102 about the entrance to passageway 112 (FIG. 3). Additionally, preferably, both the proximal and distal spacer surfaces 134,136 have defined thereon respective compression rings 140 each comprising a sharp ridge surrounding the respective depressions 132 that will, upon final assembly of subassembly 100, become pressed into the adjacent surfaces of the respective valve members 122,126 to assuredly retain the valve members precisely centered within valve seat 118. Also, preferably, side surfaces of spacer 130 have incremental distal and proximal draft angles, defining a central apex 142 that is force-fittable within the valve seat 118 by assured engagement with the valve seat sidewalls resulting in centering of the spacer transversely within valve seat 118 (as well as having previously facilitated removal of the molded spacer from its mold cavity).

As depicted in FIGS. 6 and 7, the funnel-shaped depressions 132 of the proximal cap 106, the spacer 130 and the proximal fitting (not shown) extending to passageway 138 preferably are so sized and dimensioned as to provide a clearance and be unengaged by the deflected slit-adjacent valve portions during insertion, advancement and retraction of the guidewire through the slits of the valves, so that the valve arrangement may accommodate a range of guidewire sizes. In this way, the valve discs are not compressed and therefore do not apply pressure to the guidewire during axial movement thereof through the slits. Optionally, however, the funnel-shaped depressions could be shaped and dimensioned to prevent overdeflection of these valve portions.

The present invention is useful with guidewires ranging in size from 0.018 in (0.457 mm) to 0.038 in (0.965 mm) or more, with either a straight distal tip or a J-shaped tip. For very small diameter guidewires having a J-shaped tip, optionally a cannula (not shown) may be used to extend through the valve or valves to assure that the J-shaped distal guidewire tip is held straightened to pass through the slit or slits of the valve or valves.

FIGS. 8 to 11 illustrate the centering procedure for centering the valve members 122,126 within the valve seat 118, which is preferable to optimize the benefits of easy, low friction, nonsnagging, nondamaging insertion and retraction of a guidewire through the slits 124,128. A centering tool 200 is utilized having a handle 202 and a mandrel 204 extending therefrom sufficiently small in diameter as to be inserted into the entrance 116 and the axial bore of proximal cap 106 and through the slits 124,128 of the valve members 122,126 and axial bore 138 of the spacer 130 and then to be eventually withdrawn therefrom, without causing damage to the valves.

Figure 9:
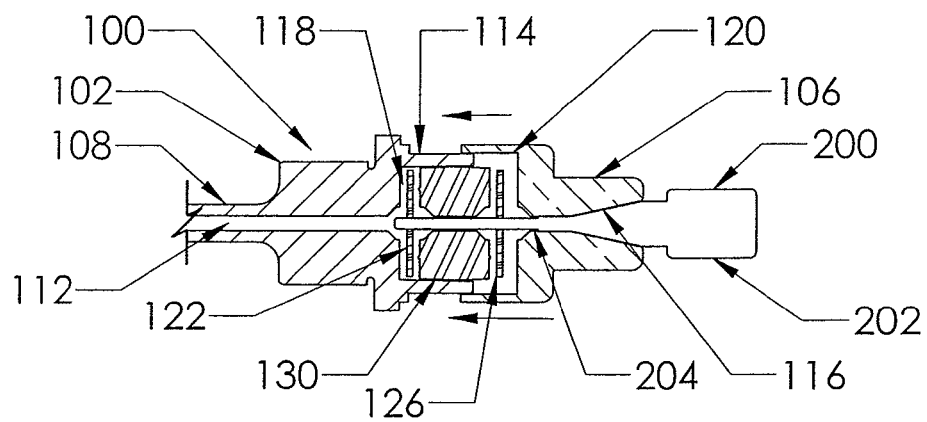
FIGS. 9 and 10 are longitudinal cross-sectional views of the proximal end assembly showing the centering tool holding the valves transversely centered before and after the proximal end cap is secured to the proximal fitting to compress the centered valves.

FIG. 9 depicts a first stage of the centering procedure during which the proximal cap 106 is not fully urged onto the proximal flange 114 of the proximal fitting 102 when the centering tool 200 is inserted therethrough, allowing the valve members 122,126 and the spacer 130 to be relatively loosely disposed in valve seat 118. Preferably, the diameters of the valve members 122,126 are less than the inner diameter of valve seat 118 thus allowing incremental transverse movement of the valve members during centering. Passage of mandrel 204 through the slits 124,128 of the valve members 122,126 perforce centers the relatively loose valve members within valve seat 118, or more accurately stated, centers the slits such that each slit 124,126 traverses a point aligned with the center of at least the conduit passageway 112.

Figure 10:
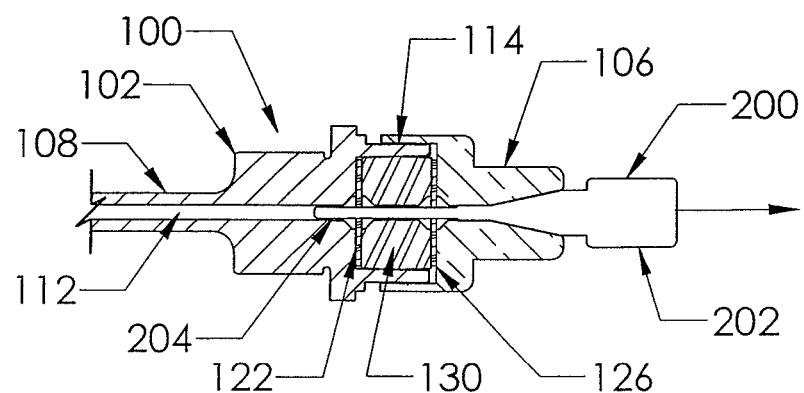

In the second stage shown in FIG. 10, the proximal cap 106 with centering tool 200 are together urged fully onto proximal flange 114 of proximal fitting 102, while the mandrel 204 maintains the valve members 122,126 precisely centered. Compression rings 140 of the proximal and distal surfaces 134,136 of spacer 130 now are pressed into the adjacent surfaces of the valve members, thus firmly securing the valve members in their precisely centered positions while proximal cap 106 is bonded or ultrasonically welded onto proximal fitting 102. Optionally, similar compression rings may be provided on the valve-adjacent surfaces of proximal fitting 102 and proximal cap 106, for similar reasons.

Figure 11:
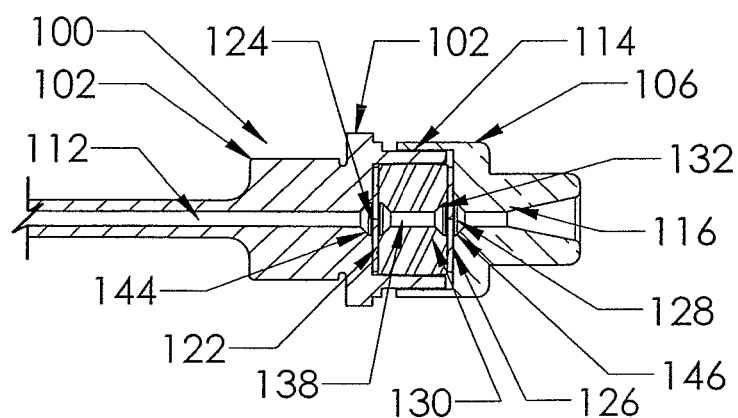
FIG. 11 is a longitudinal cross-sectional view of the proximal end assembly showing the valves fully centered and the centering tool removed.

Centering tool 200 is then removed from the subassembly, with the centered and compressed valve members 122,126 held securely in position during tool removal and thereafter, as seen in FIG. 11. With slits 124,128 now precisely traversing points axially aligned with the centers of the conduit passageway 112 and axial bore 138 of spacer 130 and the axial bore of proximal cap 106, a guidewire (see FIG. 1) can now be inserted therethrough with ease. Proximal fitting 102 and proximal cap 106 preferably include funnel-shaped centered depressions 144,146 aligned with similar depressions 132 of spacer 130 to facilitate insertion of the guidewire into and through the respective axial bores and passageways, and also provide clearances for lips of the valve members adjacent their slits 124,128 to be deflected thereinto when, firstly, the centering tool mandrel is being urged through slits 124,128 and then withdrawn, and subsequently, a guidewire is being inserted therethrough or retracted therefrom, and while the guidewire is in position.

The dimensions or diameters of the respective axial bores and passageways of the components of the subassembly, and the length of the slits of the valve members, are such as to permit use therewith of a range of guidewire diameters. The material for valve members may be, for example, silicone, but is preferably, polyisoprene such as Part No. 600X600X016-30POE sold by Apple Rubber Products, Inc. of Lancaster, N.Y. Alternatively, other materials may also be utilized. The thickness of the valve members is preferably about 0.016 in (0.406 mm), and that the length of each slit is generally about 0.060 in (1.52 mm). Further, it is preferred that at least 0.010 in (0.254 mm) clearance is provided between the edges of each valve member on all sides and the inner surface of valve seat. Preferably, also, the valve members are identical for simplification of assembly procedures. Optionally, a small amount of silicone oil may be used within the valve seat for lubrication of the valves that may facilitate insertion, advancement and retraction of the guidewire.

It will be appreciated by those skilled in the art that changes could be made to the embodiments described above without departing from the broad inventive concept thereof. For example, the valve seat could be defined in the proximal cap; also, the proximal cap could have a distally projecting flange received into a recess of the proximal fitting; further, the valve openings could be a cross-shaped pattern of slits, or other pattern of intersecting slits, or an annular hole of small diameter. It is understood, therefore, that this invention is not limited to the particular embodiments disclosed, but it is intended to cover modifications within the spirit and scope of the present invention as defined by the appended claims.

What is claimed is:

1. A method of centering at least one valve within a valve seat of a medical device, comprising the steps of:
   positioning at least one valve within the valve seat of the medical device such that each of the at least one valve is transversely oriented within the valve seat with a diameter less than an inner diameter of the valve seat and a center opening to be aligned with a passageway of the medical device;
   positioning a cap on the medical device adjacent the valve seat in an initial position wherein an aperture defined by the cap is aligned with the device passageway and the at least one valve adjustably positioned between the device and the cap;
   positioning a mandrel of a centering tool through the aperture of the cap, through the center opening of the at least one valve and at least partially into the device passageway such that the at least one valve is transversely adjusted to a position within the device wherein the center opening is aligned with the device passageway;
   affixing the cap to the medical device in a second position such that the at least one valve is axially compressed between the cap and the device such that the at least one valve is fixed in position relative to the valve seat; and
   withdrawing the centering tool from the device.

2. The method of claim 1, wherein transverse valve-adjacent surfaces of the device include compression rings that become pressed into the at least one valve upon complete assembly to securely retain the at least one valve in position relative to the valve seat upon withdrawal of the centering tool from the device.

* * * * *